United States Patent [19]

Barshad et al.

[11] Patent Number: 5,416,579
[45] Date of Patent: May 16, 1995

[54] METHOD FOR DETERMINING CONCENTRATION IN A SOLUTION USING ATTENUATED TOTAL REFLECTANCE SPECTROMETRY

[75] Inventors: Yoav Barshad; Yael S. Barshad, both of Arnhem, Netherlands

[73] Assignee: Nova Chem BV, Netherlands

[21] Appl. No.: 278,292

[22] Filed: Jul. 21, 1994

Related U.S. Application Data

[63] Continuation-in-part of Ser. No. 96,323, Jul. 23, 1993, abandoned.

[51] Int. Cl.$^6$ .............................................. G01J 3/42
[52] U.S. Cl. ..................................... 356/300; 356/328
[58] Field of Search ............... 356/300, 133, 319, 326, 356/328

[56] References Cited

U.S. PATENT DOCUMENTS

| | | | |
|---|---|---|---|
| Re. 33,064 | 9/1989 | Carter et al. | 356/417 |
| 3,282,149 | 11/1966 | Shaw et al. | 356/133 |
| 3,433,570 | 3/1969 | Hansen | 356/128 |
| 4,427,293 | 1/1984 | Harmer | 356/133 |
| 4,564,292 | 1/1986 | Omet | 356/133 |
| 4,600,310 | 7/1986 | Cramp et al. | 385/12 |
| 4,639,594 | 1/1987 | Schoch et al. | 356/133 |
| 4,806,013 | 2/1989 | Bodenheimer et al. | 356/133 |
| 4,818,710 | 4/1989 | Sutherland et al. | 250/365 |
| 4,827,121 | 5/1989 | Vidrine, Jr. et al. | 356/133 |
| 4,834,533 | 5/1989 | Horike et al. | 356/133 |
| 5,055,699 | 10/1991 | Konig et al. | 356/133 |
| 5,070,243 | 12/1991 | Bornstein et al. | 356/133 |
| 5,097,129 | 3/1992 | de Vries et al. | 250/339 |

FOREIGN PATENT DOCUMENTS 111423 7/1982 Japan ....................................... 356/51

OTHER PUBLICATIONS

Simhony et al, Analytical Chemistry, vol. 60, No. 18 Sep. 15, 1988, pp. 1908–1910.

*Primary Examiner*—F. L. Evans
*Attorney, Agent, or Firm*—M. Lukacher

[57] ABSTRACT

A method for analyzing fluids, particularly the solute concentration in liquids which are dense or viscous and are only slightly transparent to light, which utilizes an attenuated total reflectance cell with a curved-path optical wave guide, particularly an optical fiber, the wave guide having a portion of its surface interfacing with the fluid to be analyzed. The wave guide has selected dimensions and properties including bend radius, waveguide radius, index of refraction, and effective light path which optimize the measurement. The optimum wave guide dimensions and wavelength of light are selected through calibration of the ATR device with a plurality of fluids of known composition. Light is transmitted through the wave guide and is attenuated by partial reflectance within the wave guide due to absorbance by the fluid being analyzed. The attenuated transmittance is related to optical absorbance, which is correlated directly to concentration of solute.

5 Claims, 3 Drawing Sheets

METHOD FOR DETERMINING CONCENTRATION IN A SOLUTION USING ATTENUATED TOTAL REFLECTANCE SPECTROMETRY

DESCRIPTION

This a continuation-in-part of an application, Ser. No. 08/096,323, filed Jul. 23, 1993, now abandoned.

The present invention relates to a method for determining concentrations of solutions by a spectrometry system combining a curved-path attenuated total reflectance cell and an optical spectrometer.

The invention is especially suitable for use in analyzing the concentration of solutes in liquids, particularly liquids which are dense or viscous, such as many aromatics, paints, and liquors, and which are only slightly transmissive of light.

The invention is based upon the principle that the optical absorption of a fluid to be analyzed can be measured in terms of the attenuated total reflectance of light in a cell having an optically conductive element or wave guide with a surface interfacing the fluid under analysis. We have found further that the optical absorbance of a fluid under certain test conditions is related directly to the solute concentration of the fluid.

The absorbance of light within a few layers of molecular thickness at the interface between the fluid and the wave guide attenuates the total reflectance variably across the spectrum of the light conducted through the element. Either broad-spectrum or monochromatic light can be used. For monochromatic light, only a simple photoreceptor system is required to determine the intensity of the attenuated beam emergent from the wave guide. For broad-spectrum incident light, an optical spectrometer is used to obtain the output spectrum, from which the intensity may be determined at any desired wavelength. The latter permits selection of an optimum wavelength for analysis of the fluid, based in part upon the degree of light absorption in the wave guide.

While the invention is especially suitable for liquid measurements, it is applicable, through the use of confinement devices which may contain pressurized gases, to analyze gaseous fluids.

Accordingly, it is a principal object of the invention to provide an improved method utilizing an attenuated total reflectance (ATR) cell and an optical spectrometer for determining the concentration of solute in a fluid in either a static containment cell or a flow through cell through which the fluid passes during analysis.

Briefly described, a spectrometry system for use in a method of measuring the concentration of a fluid in accordance with the invention is provided with a cell, including a container for a fluid to be analyzed and a light-conducting element or wave guide in the container. The wave guide has a surface interfacing with the fluid in the container and is preferably a curved rod or fiber, with curvature of preferably about 180 degrees, over that portion in contact with the fluid. The radius of curvature of the waveguide, the radius of the wave guide element itself, and the ratio of the two radii are parameters of the system, which are selected to optimize sensitivity of the concentration measurement.

The wave guide further provides an optical path having light input and output terminals between which a beam of light propagates. The system has means for applying light to the input terminal. Light travels within the wave guide to the output end, and in so traveling undergoes successive partial reflections from the interfacing surface within the curved wave guide. The intensity of the beam appearing at the output terminal represents the resultant internal reflectance of the beam in the wave guide, the beam intensity having been attenuated variably across the spectrum of the light in accordance with the optical absorption characteristics of the fluid being analyzed and the dimensions and optical characteristics of the wave guide. An optical spectrometer optically connected to the wave guide, and having input optics and an optical spectrum generator and analyzer, provides a spectrum containing information as to the characteristics of the fluid which are of interest, particularly its concentration.

To permit determination of the concentration of solute in a fluid of unknown concentration, a plurality of calibration curves is generated by measuring transmittance through the ATR cell of several solutions of the fluid having differing known concentrations of the solute, when using several waveguides having differing bend radius ratios. By transmittance is meant the intensity of the attenuated beam which leaves the output end of the wave guide. From these curves, and an estimate of the concentration to be determined, the optimum waveguide and wavelengths which maximize the ATR's sensitivity are selected. The fluid of unknown concentration is then analyzed using the optimum waveguide. From the value of the transmittance of the waveguide at the selected wavelength of light, the concentration of solute is inferred.

The method according to the invention is particularly useful, for example, in continuously monitoring the composition of paints or other nearly opaque fluids (generally, materials with very high absorbances at specific wavelengths) during manufacture, using an ATR device having a flow-through cell.

The foregoing and other objects, features, and advantages of the invention will become more apparent from a reading of the following description in connection with the accompanying figures in which FIG. 1 is a schematic diagram of a spectrometry system for use with the method of the invention;

Figure 1:
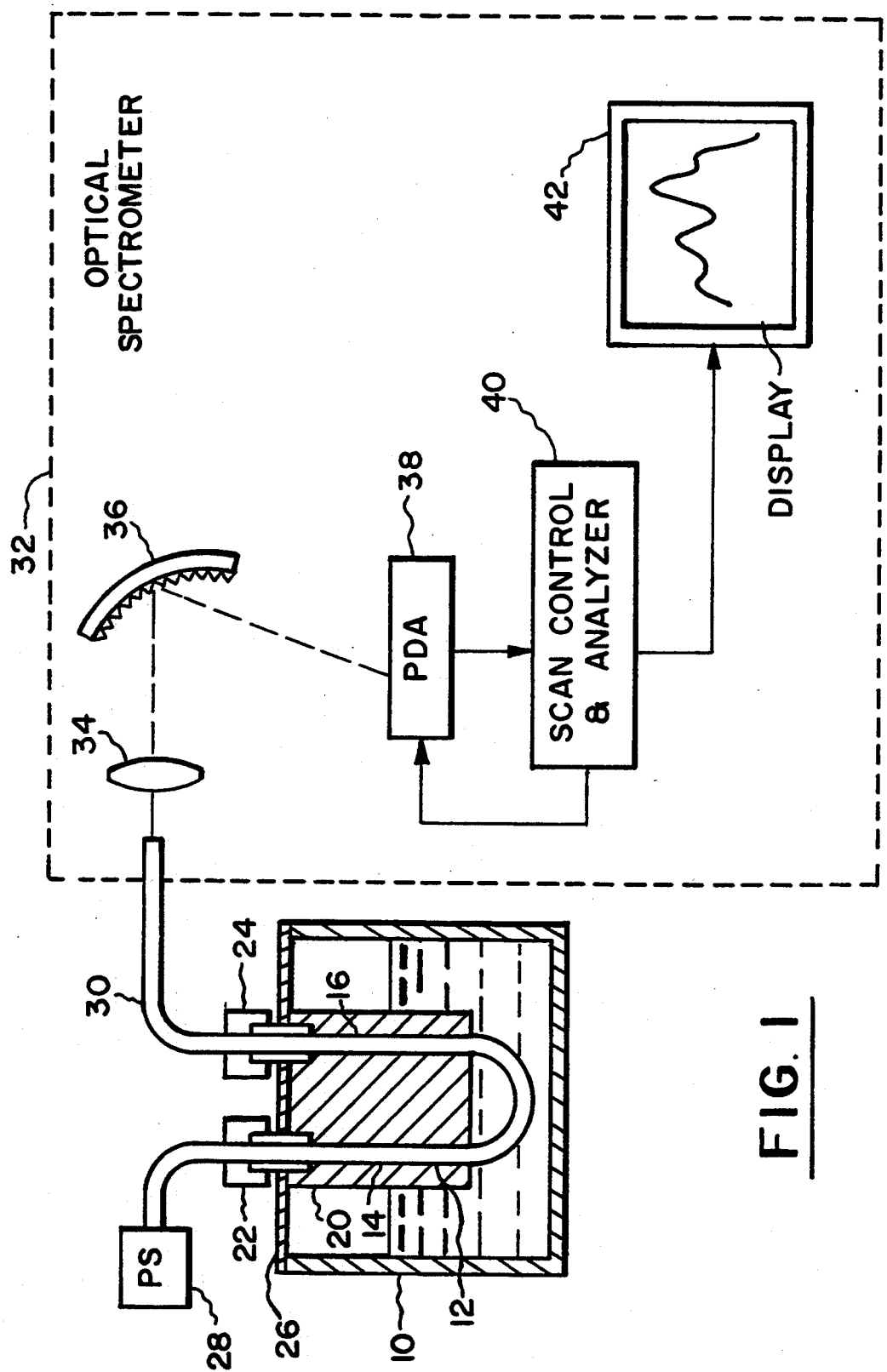

Referring more particularly to the figures, there is shown in FIG. 1 an ATR cell 10 for containing the fluid (particularly a liquid) to be analyzed. The cell 10 may contain a quantity of the liquid statically therein or the liquid can flow through the container. Cell 10 contains a light-conducting element or wave guide 12 in the form of a U-shaped optical fiber or rod having straight sections 14 and 16 and an arcuate, preferably circular, section 18 which has a surface interfacing with the liquid in cell 10. Wave guide 12 may be a conventional clad glass fiber from which the cladding is removed or stripped at least in the arcuate section 18 thereof. The light-conducting element in the cell may alternatively be provided by various light transmissive rods or U-shaped elements of glass or quartz.

A support body in the form of a cylinder of stainless steel 20 has holes therein through which sections 14 and 16 of element 12 extend. Opposite ends of the element provide light input and output terminals and may be contained in optical fiber connectors 22 and 24. These may be connectors of the type which are commercially available and known as SMA connectors. The connectors and support body 20 are attached or captured to a cover plate or bar 26 on the top of container 10.

The connector 22 may have a light source such as a broad spectrum lamp, for example a xenon lamp which may be pulsed by pulses from an oscillator pulse generator power supply 28. Other broad spectrum sources may be used, for example, certain light emitting diodes or laser diodes which are swept in frequency across an operating range. Preferably the range which is covered is the entire visible range or a significant portion thereof, e.g., 100 or more nanometers. Output terminal connector 24 has an output fiber 30 which directs light to the optical spectrometer 32. Instead of an output fiber 30, other optics such as a mirror or other light deflectors may be used.

Alternatively, a monochromatic input light source such as a laser (not shown) can be used. The wavelength selected must be absorbable by the fluid to be analyzed. When such a match is available, only a simple photodetector and its electronic controls is required to measure the intensity of the output beam, instead of spectrometer 32. However, a system with an optical spectrometer is preferred, since the device is then able to analyze any fluid which absorbs light of any wavelength within the full range of the instrument. The flexibility of such a system to choose alternate wavelengths is highly useful, as described hereinbelow, in helping to select the radius parameters of the wave guide.

Light propagates through element 12 by multiple internal reflections. In section 18, where the interface between the fluid and the light conducting material exists, the reflectance is attenuated variably by partial reflections across the spectrum of the input light in accordance with the optical absorption characteristics of the fluid in cell 10. The spectrum at the output terminal 24 therefore contains information respecting the absorption characteristics of the fluid material. The optical spectrometer 32 provides a display reflecting this information and from which characteristics of interest of the fluid, such as concentration of solute, can be determined.

An important characteristic of a curved-path wave guide is the parameter D, defined as the ratio of the bend radius of the wave guide to the radius of the wave guide itself. If this ratio is relatively high, e.g., above about 50, sensitivity can be reduced because of too few internal partial reflections; whereas, if D is relatively low, e.g., below about 10, the light beam can be too greatly attenuated because of too many internal partial reflections, leading to a low and noisy output signal.

The selection of a wave guide having optimum operating range and sensitivity depends on not only its D value, but also on the optical absorbance of the wavelength of light in the fluid being analyzed, and on the concentration of solute in the fluid, as described hereinbelow.

In normal absorption spectroscopy, the optical absorbance (A) is defined as the negative logarithm of the transmittance (T):

$$A = -\log(T) \quad (1)$$

We found that in ATR spectroscopy T is a very strong function of the number of reflections z, which varies with λ (The linear relationship is with $\sqrt[z]{T}$), the geometry of the waveguide and the acceptance cone at the input end or terminal of the waveguide. This quantity maintains a linear relationship with concentration over significant ranges. The acceptance cone is well known and depends upon the index of refraction of the material of the waveguide. The number of reflections is determined by the geometry of the waveguide and particularly the radius of curvature of the waveguide in the bend 18 and the radius of the waveguide across its cross-section. z is determined by geometrical ray tracing and varies typically from 2 to 10. The relationship between concentration or absorbance and the transmittance in absorption ABS units is as follows:

$$ABS = -\log(\sqrt[z]{T}) = -\log(T^{1/z}) \quad (2)$$

The "effective path" ($P_{eff}$) of light in the interface between the wave guide and the fluid, where λ is the wavelength of the light in the guide 12, $n_1$ is the index of refraction of the fluid, $n_2$ is the index of the waveguide material and α is the angle of incidence of the ray of light on the interface is with appropriate simplification as follows:

$$P_{eff} = \frac{n_1 - \lambda \cdot \cos d}{\pi \cdot n_2 \cdot (1 - n_1^2) \cdot (\sin^2 \alpha - n_1)^{\frac{1}{2}}} \quad (3)$$

We have found further the following relationship among transmittance (T), wavelength (λ), effective path ($P_{eff}$), and concentration (C):

$$ABS = -\log(\sqrt[z]{T}) = 1 - \lambda \cdot P_{eff} \cdot C \quad (4)$$

Figure 2:
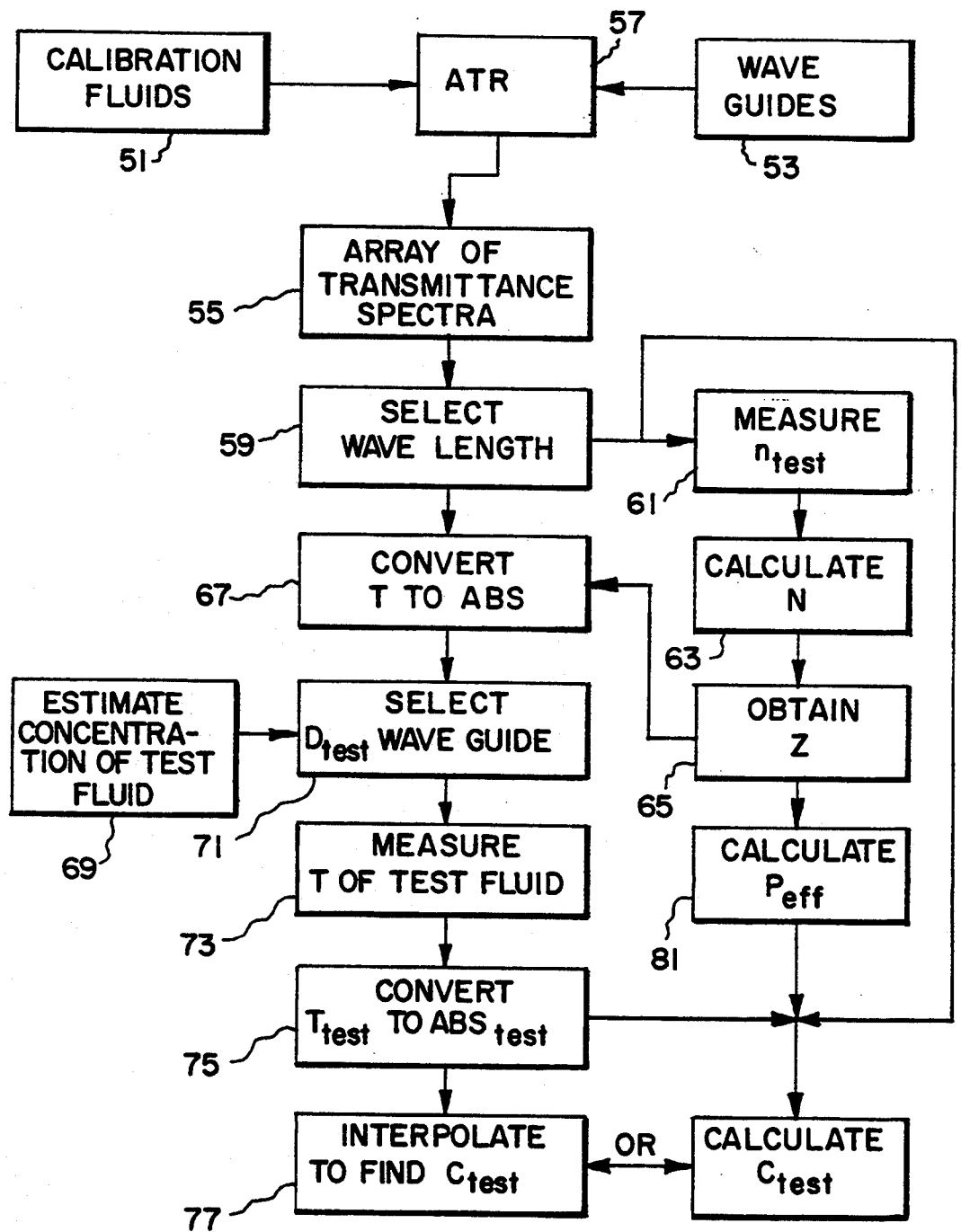
FIG. 2 is a flow diagram of a method of the invention.
Figure 3:
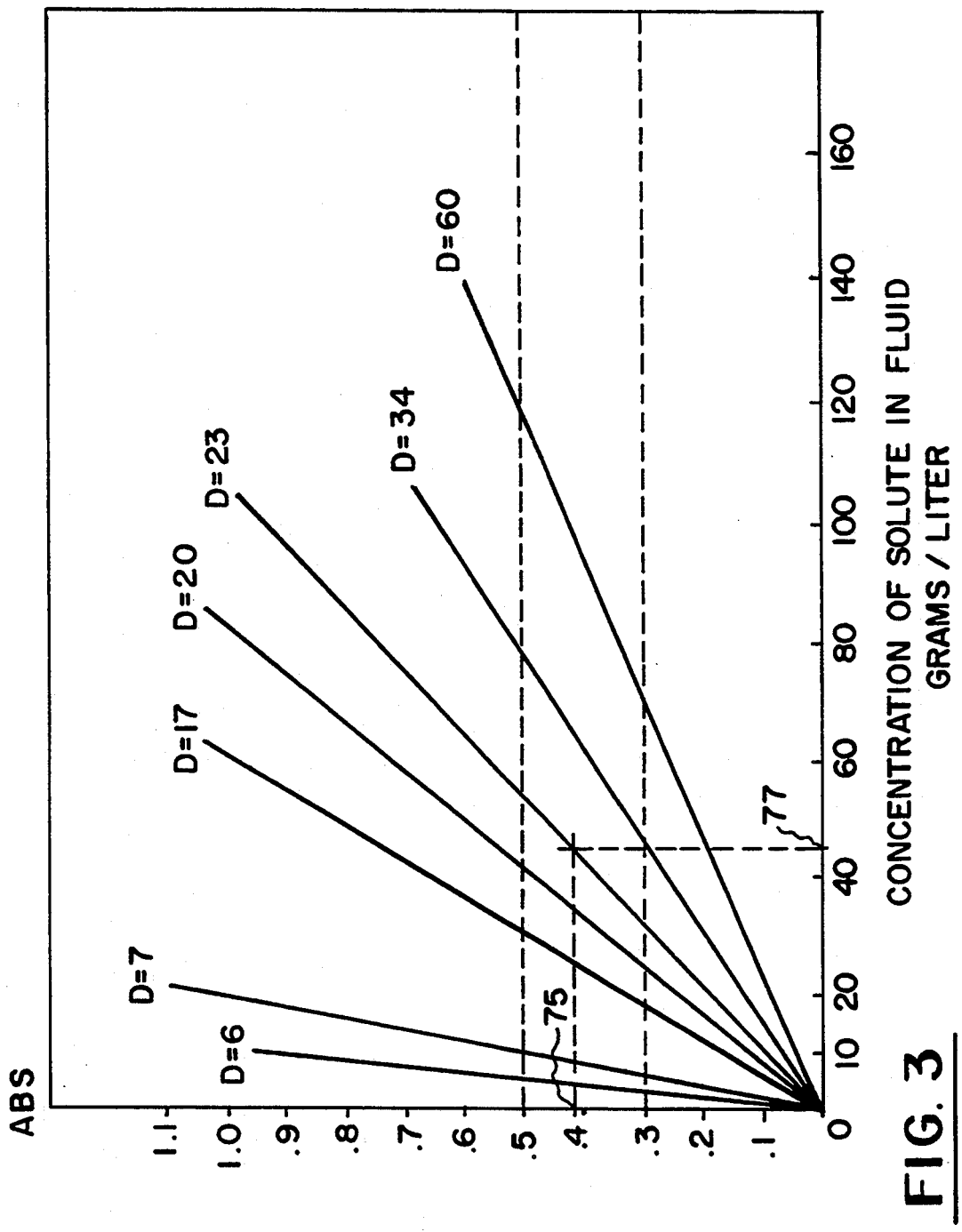
FIG. 3 is a graph of calibration curves for a typical use of the invention, showing optical absorbance as a function of solute concentration for a plurality of waveguides having different bend radius ratios.

A method for determining the concentration of solute in a fluid of unknown concentration (the "test fluid") using an ATR spectrometer (ATR), illustrative of the invention, is shown in FIG. 2:

a) A plurality of fluids 51, typically four to six, having different known solute concentrations is prepared from the same solute and fluid materials as the test fluid ("calibration fluids").

b) A plurality of wave guides 53, typically two to six, having different known D values is provided.

c) An array of transmittance spectra 55 is generated by the ATR 57 for all combinations of calibration solutions and wave guides.

d) A wavelength of light 59 for analysis is selected from the spectra which provides high optical absorbance under all calibration combinations.

e) The index of refraction of the test fluid ($n_{test}$) 61 at the selected wavelength 59 is measured, N 63 is calculated using the known index of refraction of the wave guide material to be used, and z 65 is obtained by ray tracing.

f) Values of ABS 67 are calculated according to Equation (2) for all the transmittance values 55 obtained at the selected wavelength 59. These ABS values can be plotted against the values of the concentrations of the calibration fluids 51 as a function of D values of the wave guides 53, as shown in FIG. 3.

g) An estimate is made of the unknown concentration 69 of solute in the test fluid, and a wave guide 71 is selected having a D value ($D_{test}$) which will provide a range of response of the ATR preferably between ABS values of about 0.3 and 0.5 over a range of concentrations which include the estimated unknown concentration. If none of the available wave guides properly brackets the concentrations of interest over these ABS values, a wave guide having a smaller D value can be selected and the wavelength also changed, which will have the effect of changing the slope of the newly-selected D curve, extending its range of sensitivities over a greater range of concentrations (effectively detuning somewhat the determination by selecting a less-absorbed λ to lower the slope of D). The capability to alter wavelength selection to position the estimated test value more favorably in the ATR sensitivity range is a great advantage of using broad-spectrum input light and an optical spectrometer to analyze the output of the cell.

h) The ATR is equipped with the $D_{test}$ wave guide, the test fluid is placed in the cell container, transmittance is measured at the selected wavelength, and the transmittance value ($T_{test}$) 73 is converted to an absorbance unit value ($ABS_{test}$) 75 by means of Equation (2).

i) The concentration of solute in the test fluid can be inferred, or confirmed by interpolation 77 of $ABS_{test}$ in the calibration curve for the $D_{test}$ wave guide, or the concentration can be calculated 79 directly from Equation (4) after the effective path ($P_{eff}$) 81 is determined according to Equation (3), but is preferably obtained from the curves of FIG. 3 by interpolation.

EXAMPLE

Seven solutions of Acid Green 6 (CI Number 42095) were prepared respectively at the following concentrations, using water as the fluid: 10, 20, 40, 60, 80, 100, 120 grams per liter.

Seven glass waveguides were provided, having index of refraction of 1.50 and D values of 5, 7, 17, 20, 23, 34, and 60, respectively.

An ATR spectrometer, such as a device disclosed by Bodensteiner in U.S. Pat. No. 4,806,013, was equipped successively with each wave guide, and transmittance spectra were obtained for each of the seven fluids, a total of 49 combinations.

A test wavelength of 640 nm was selected, and transmittance values at that wavelength for each of the combinations were converted to ABS values, using Equation (2). These ABS values were plotted against their respective concentration values, as shown in FIG. 3.

A test fluid sample was estimated to have a solute concentration of about 46 grams per liter, so the wave guide having a D value of 23 was selected for the analysis, since its ABS range between 0.3 and 0.5 encompasses concentrations between about 27 and 53 grams per liter. This wave guide has a z value of seven.

The index of refraction of the test fluid was determined to be 1.333, using a Toga (Japan) Refractometer, and N was calculated to be 0.887.

The ATR was equipped with the D=23 wave guide, the test fluid was placed in the cell container, and a transmittance value at the test wavelength was obtained. The transmittance value was converted to an ABS value of 0.41, using Equation (2). Interpolation of this ABS value in FIG. 3 yielded a test fluid solute concentration of 44 grams per liter.

From the foregoing description, it will be apparent that there has been provided a method for determining the concentration of solute in a fluid utilizing a cell operative on the basis of attenuated total reflectance (ATR). Variations and modifications in the herein described method, within the scope of the invention, will undoubtedly suggest themselves to those skilled in the art. Accordingly, the foregoing description should be taken as illustrative and not in a limiting sense.

What is claimed is:

1. A method of using an attenuated total reflectance (ATR) spectrophotometer having an optical wave guide with a curved optical path to determine concentration of solute in a test fluid of unknown concentration, comprising the steps of:
   a) providing a plurality of optical wave guides for said ATR spectrophotometer having differing values of D, where D is the ratio of the bend radius of said optical wave guide to the radius of said optical wave guide, each of said plurality of wave guides having an index of refraction greater than that of said fluid of unknown concentration, and each of said wave guides having a characteristic effective path ($P_{eff}$) and a characteristic number of internal reflections (z) for light of a given wavelength;
   b) providing a plurality of calibration fluids comprising the materials of said solute and test fluid at differing known concentrations of solute (C);
   c) determining values of transmittance (T) in said ATR spectrophotometer when combining each of said known concentrations with each of said optical wave guides having differing values of D;
   d) calculating absorbance units (AU) for each of said combinations of C and D according to the equation:

$$AU = -\log(T^{1/z});$$

e) selecting a wavelength of light (λ) for said determination;
   f) measuring the index of refraction of said test fluid at said selected wavelength of light;
   g) selecting an operating range of said concentration values to be determined by said ATR spectrophotometer;
   h) selecting an optical wave guide for said ATR spectrophotometer having a D value ($D_{test}$) which provides AU values in the working range of sensitivities of said ATR spectrophotometer over said operating range of said concentration values;
   i) immersing said selected optical wave guide having said $D_{test}$ value in said fluid of unknown concentration;
   j) determining the AU value for said fluid; and
   k) comparing said AU value for said fluid to said values of AU determined for said calibration fluids with said element having said $D_{test}$ value to determine the value of said solute concentration in said fluid of unknown concentration.

2. The method of claim 1 wherein said working range of sensitivities is between about 0.1 and about 0.7 ABS units.

3. The method of claim 1 wherein said working range of sensitivities is between about 0.3 and about 0.5 ABS units.

4. The method of claim 1 further comprising the step of confirming said value of said solute concentration in said fluid of unknown concentration by calculating said value according to the equation:

$$ABS = -\log(^z\sqrt{T}) = 1 - \lambda \cdot P_{eff} \cdot C$$

wherein ABS is the measured value of said optical absorbance in absorbance units, $\lambda$ is said selected wavelength of light, $P_{eff}$ is the effective path of light of said selected wavelength through said selected wave guide, z is the number of internal reflections of light of said selected wavelength in passing through said selected wave guide, T is the optical transmittance measured at the output of said selected wave guide, and C is said value of said concentration of solute in said fluid of unknown concentration.

5. The method of claim 1 wherein said step of selecting an operating range includes providing an estimated value of said unknown concentration of solute to be determined.

* * * * *